United States Patent [19]
Northup

[11] 3,955,408
[45] May 11, 1976

[54] FLUIDLESS BOTTLE TESTING METHOD AND APPARATUS

[76] Inventor: John D. Northup, 2460 Underhill Road, Toledo, Ohio 43615

[22] Filed: Sept. 8, 1975

[21] Appl. No.: 611,530

[52] U.S. Cl. .................................. 73/94; 73/100
[51] Int. Cl.² .................................... G01N 3/00
[58] Field of Search .............. 73/94, 88 R, 12, 100; 209/79

[56] References Cited
UNITED STATES PATENTS

| | | | |
|---|---|---|---|
| 3,618,370 | 11/1971 | Dubble | 73/94 UX |
| 3,628,379 | 12/1971 | Babunovic | 73/94 |
| 3,896,657 | 7/1975 | Brandt et al. | 73/12 |

*Primary Examiner*—Jerry W. Myracle
*Attorney, Agent, or Firm*—Allen Owen

[57] ABSTRACT

A fluidless bottle testing method and apparatus are disclosed. After being subjected to a squeeze test for side wall strength, bottles are moved to a bottle bottom tester which places the outer surfaces of the bottom and of the lower side wall of the bottle into tension. Bottles which would fail in service due to thin or weak walls, checks and scratches fail during the test and are thus removed prior to filling. Preferably the apparatus for performing the bottom test supports the bottle at a large bead on the neck or annularly at the lower portion of the side wall. A test rod is lowered (or the bottle is raised) into the mouth of the bottle and ultimately against the central bottom of the bottle, creating a flexure stress in the bottle bottom. The test facilitates rapid 100% bottle testing without the application of pneumatic or hydrostatic pressure to the interior of the bottle.

9 Claims, 6 Drawing Figures

U.S. Patent   May 11, 1976   3,955,408
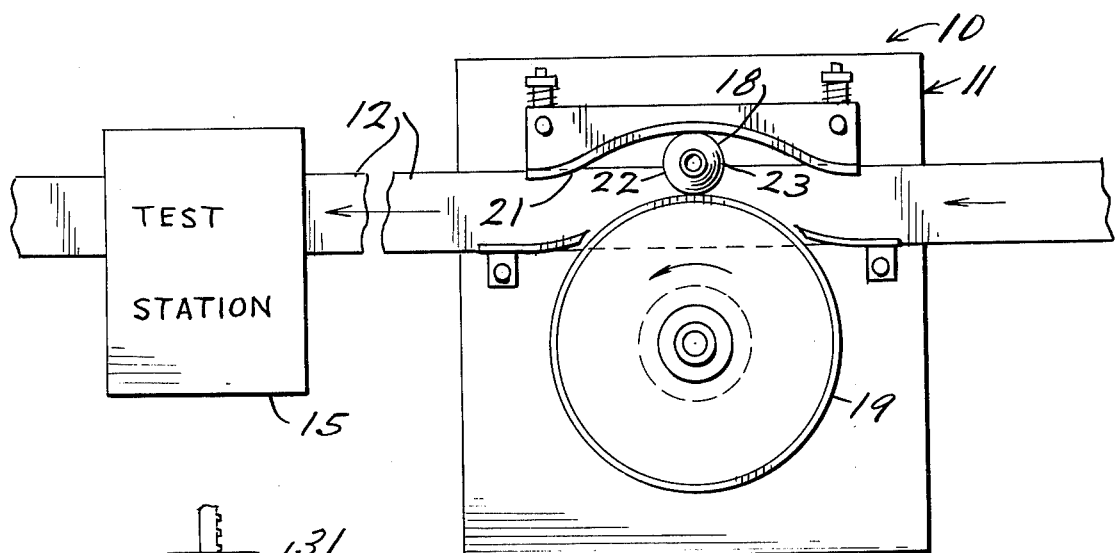
FIG-1-
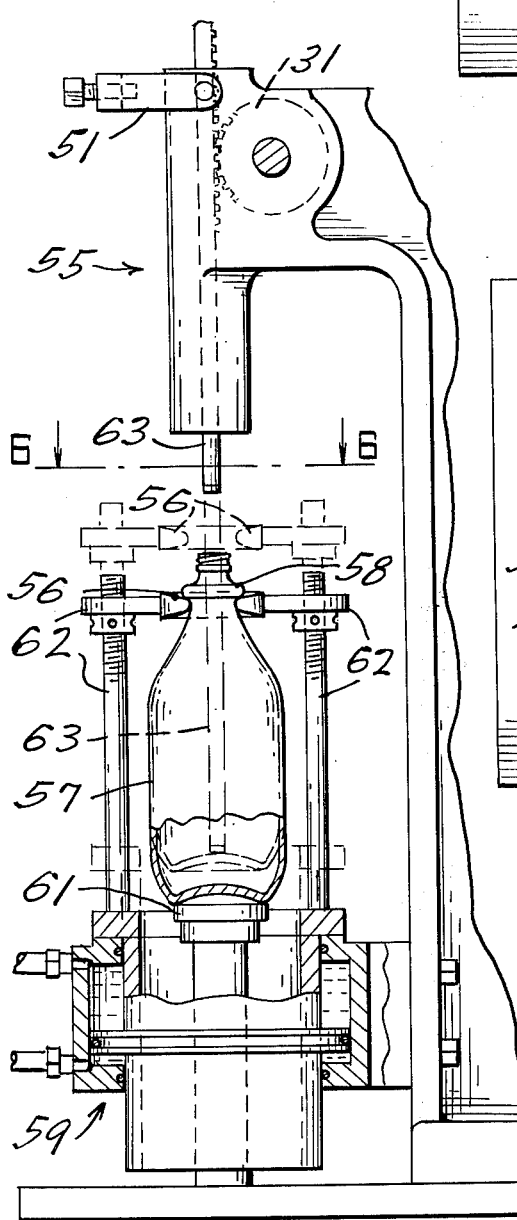
FIG-5-
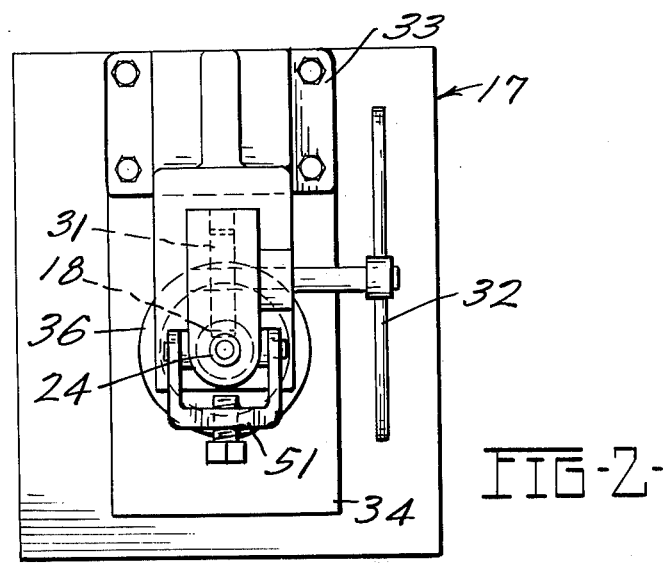
FIG-2-
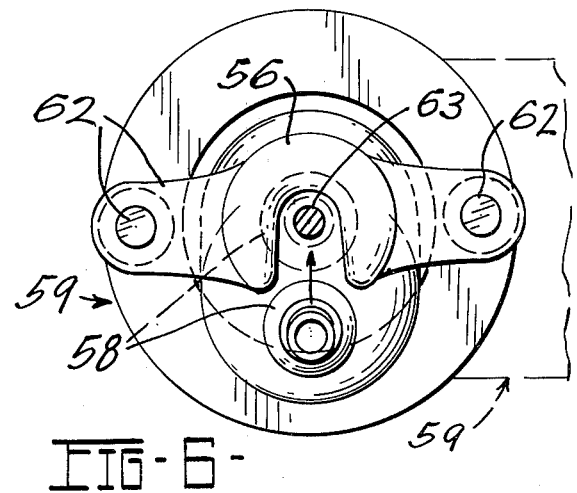
FIG-6-

U.S. Patent   May 11, 1976   Sheet 2 of 2   3,955,408
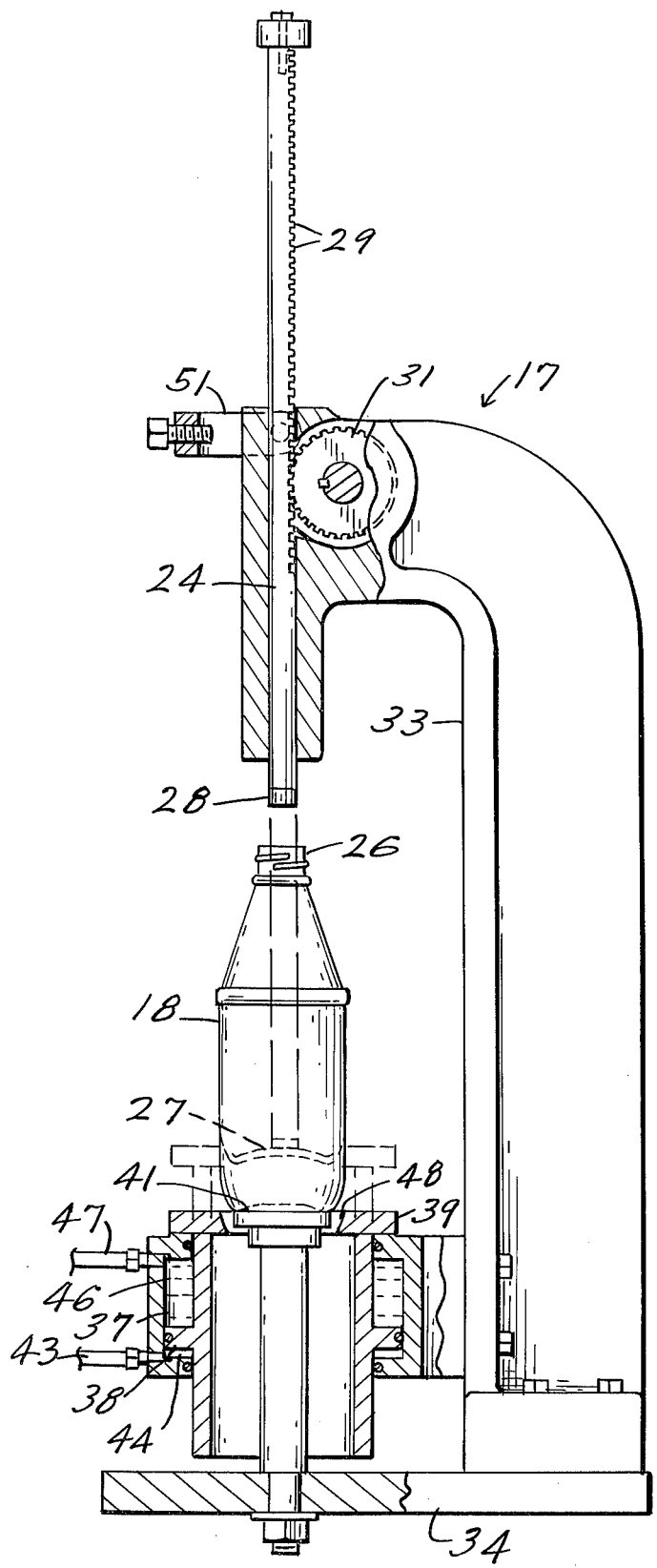
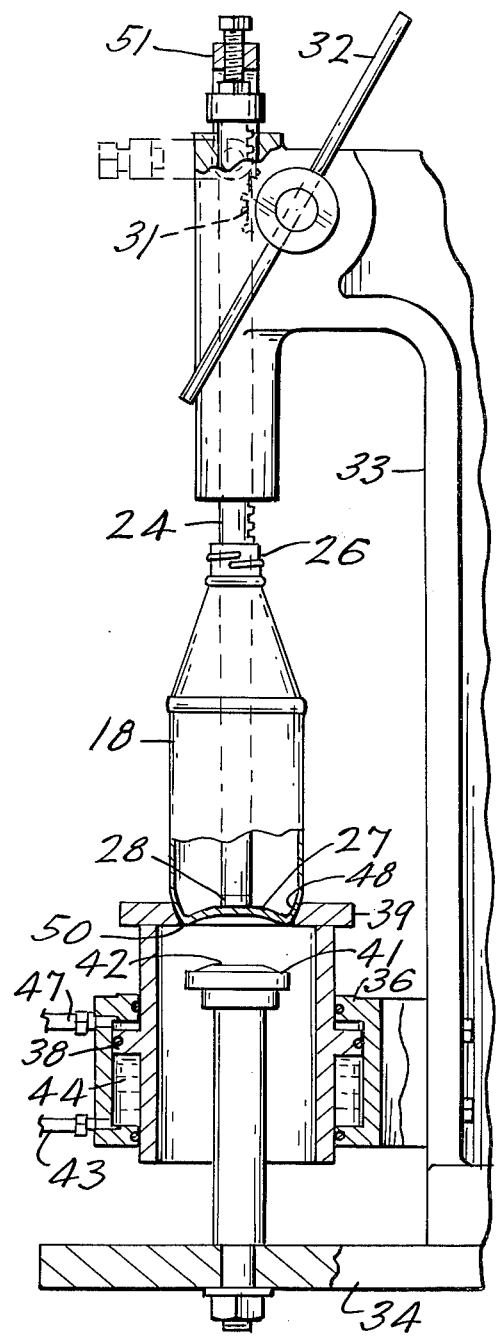
FIG-3-   FIG-4-

FLUIDLESS BOTTLE TESTING METHOD AND APPARATUS

BACKGROUND OF THE INVENTION

The invention relates to glass bottle testing, and more particularly to a totally mechanical test which eliminates the need for pneumatic or hydrostatic pressure.

Glass bottles designed to hold carbonated beverages are pressure vessels which under certain conditions must withstand substantial pressure. In order to assure the safe performance of each and every glass bottle going into service, some practicable means for testing all of the pressure containers is necessary.

Glass in the form used for the manufacture of bottles is very strong in resistance to compression stresses but very weak in resistance to tension stresses. This is evidenced by the fact that flat glass breaks evenly along a scratch when the side of the glass having the scratch is placed in a small degree of tension. Annealing procedures normally used in the production of glass bottles cause the outside surface of the bottles to assume a state of compression, while the inside surfaces of the bottles are in tension. This effect results primarily from the fact that when a bottle mold opens, the inside surface of the bottle is hotter than the outside surface. The inside surface thus tends to draw the bottle inward upon cooling, shrinking it slightly and placing the outside surface in compression, but of course not shrinking the bottle sufficiently to avoid tension on the inside surface. Bottles so produced are thus able to withstand a certain amount of abrasion and internal pressure without failure, since the outside of the bottle remains in compression.

As is well known in the bottle manufacturing industry, some glass bottles do develop small and even microscopic scratches, checks and abrasions on their outside surfaces between the time they are removed from the mold and the time they are deposited in shipping cases. Often these blemishes are in the bottom because the bottles are transported on their bottoms from one conveyor to another, through annealing ovens and through mechanical, electrical and optical inspection equipment. If such a check, scratch or abrasion goes undetected and the bottle is filled with a product capable of developing pressure, the internal pressure under certain conditions can cause the normal compressive stress on the outside surface of the bottle to be replaced with a tensile stress. Only a small degree of such tensile stress at the location of the blemish will cause the bottle to fail, sometimes causing severe damage and injury. Therefore, to effectively test a glass bottle, critical areas of the bottle's outside surface should be put into tension.

In order to create external tensile stress in a glass bottle during testing, internal test pressure may be used. Compressed air is objectionable, however, since a bottle failing the test will explode with considerable force, throwing glass fragments at high velocity. Compressed air testing is therefore not commonly used for testing because of safety considerations. Even if bottles are enshrouded in connection with compressed air testing to avoid the dangers of flying glass fragments, the procedure is still unsatisfactory since flying glass fragments are extremely abrasive and can quickly wear away any material used to enshroud a bottle.

The general practice in the glass bottle manufacturing industry is presently to withdraw a certain percentage of sample bottles and to test them by filling them with water and subjecting them to hydrostatic pressure. Although this type testing is satisfactory when sample testing is sufficient, it is not satisfactorily adaptable to 100% testing because a considerable amount of time is required to empty the bottle of water after testing, and because some small quantity of water is left inside the bottle even after emptying.

In my co-pending application Ser. No. 497,751, now U.S. Pat. No. 3,895,514, I disclose a bottle tester wherein an expandable bladder is inserted into the interior of the bottle and then filled with water or other liquid to produce a test stress in the bottle walls and bottom. The apparatus provides a reliable test and eliminates most of the problems of prior testing methods, enabling 100% testing to be implemented. However, since air must be removed from the bottle and fluid must be pumped into and out of the bladder, the method and apparatus are not as simple in structure and operation as are those of the present invention described below.

SUMMARY OF THE INVENTION

The present invention is a bottle testing method and apparatus which facilitate 100% testing of glass bottles in a fast and efficient manner without wetting the inside of the bottles and without the use of any pressure fluid. The bottle test of the invention utilizes a novel apparatus which tests the bottom, the bearing surface and the lower part of the side wall of a bottle, in combination with a squeeze type bottle tester which tests the side wall of the bottle. Such a squeeze testing apparatus is shown, for example, in U.S. Pat. No. 3,765,231. Applying force only to the side wall of the bottle, the squeeze tester puts the side wall of the bottle in tension through a "hinge" effect. While the bottle is compressed together from two opposed sides, the two side areas which are 90° from the compressive load points are placed in tension at their outside surfaces due to slight deformation of the bottle. The bottle is rolled through the tester so that all areas of the side walls are tested.

The apparatus of the invention complements the squeeze tester by testing the bottom, the bearing surfaces and the lower part of the side walls of a bottle. This testing is performed under the principle that since the bottom of a bottle is of slightly concave but approximately flat configuration, a force of sufficient magnitude applied to the inside center of the bottom, when the bottle is appropriately supported, will cause the unsupported outer surface of the bottom and the tapered lower side wall to develop a tension stress. The total amount of force required to break a given bottle is a measure of the resistance of the lower portions of the bottle to internal pressure.

DESCRIPTION OF THE DRAWINGS

FIG. 1 is a diagrammatic plan view showing a bottle squeeze tester used in connection with the method and the apparatus of the invention;

FIG. 2 is a plan view of an apparatus for testing the bottom areas of a bottle;

FIG. 3 is a partially sectioned elevational view of the apparatus of FIG. 2 with a bottle in a position just prior to testing;

FIG. 4 is a view similar to FIG. 2 but with the bottle being subjected to testing force;

FIG. 5 is an elevational view of an alternate form of the apparatus of FIGS. 3 and 4; and FIG. 6 is a sectional view taken along the line 6—6 of FIG. 5.

DESCRIPTION OF THE PREFERRED EMBODIMENT

FIG. 1 of the drawings schematically shows a glass bottle testing apparatus generally indicated by the reference number 10 and including a bottle side wall squeeze tester 11, conveying means 12, and a test station 15 for testing the bottom, bearing surface and lower side wall of each glass bottle. A squeeze testing apparatus such as that diagrammatically illustrated in FIG. 1 is shown, for example, in U.S. Pat. No. 3,765,231. As discussed above, the squeeze tester tests the side wall of a glass bottle 18 by rolling the bottle between a wheel 19 and a force-applying shoe 21 which subjects the side wall to a predetermined level of squeezing force. Such testing subjects the side wall, at points 22 and 23, 90° from the shoe 21, to an external surface tension, thereby causing failure of substantially all bottles which would fail in service due to weak side walls.

FIGS. 2, 3 and 4 show a simplified form of a single bottom testing unit 17 which may form a part of the multiple-unit test station 15 indicated in FIG. 1. In this embodiment, the apparatus comprises a test rod 24 which may be inserted into the neck 26 of a bottle 18 and forced against the central inside bottom 27 of the bottle. Both to protect the bottle bottom against scratching and to spread the load of the test rod 24 on the bottle bottom, avoiding point contact loading, the test rod 24 includes a somewhat resilient lower tip 28. Mechanical means are preferably employed for lowering the test rod 24 into the bottle 18, and in this embodiment, the rod includes gear teeth 29 in engagement with a circular gear 31 which rotates to move the rod 24 axially. FIGS. 2 and 4 show a manual crank handle 32 for rotating the gear 31. However, this is merely illustrative and any means may be used to rotate the gear 31 and/or to lower and raise the test rod 24. The rod 24 may even be made stationary, with mechanical means (not shown) provided to raise the bottle over the rod.

The test rod 24 and drive gear 31 are connected to a frame 33 which is in turn rigidly affixed to a base 34. Also affixed to the frame 33 is a hydraulic cylinder 36, within the fluid chamber 37 of which is received a piston 38 which supports a test stand 39 for the bottle 18. There may also be provided, affixed to the base 34, a bottle supporting pedestal 41 for receiving the bottle 18 prior to testing. As indicated in FIG. 3, the upper surface of the bottle test stand 39 and the pedestal 41 are initially at approximately the same level so that the bottle 18 may be slid from a conveying means onto the pedestal 41, which may include a bottle centering protrusion 42 as indicated in FIG. 4. The protrusion 42 helps position the bottle so that its mouth 26 is directly under the end of the test rod 24. Other alternative positioning means may be employed, such as a bottle side wall gripper (not shown) which deposits the bottle in the test stand 39, eliminating the need for the pedestal 41.

The bottle test stand 39 is raised and lowered by the hydraulic cylinder 36. To raise the stand, fluid is pumped through a hydraulic line 43 into a space 44 below the piston 38, causing fluid in the space 46 above the piston 38 to exit through a second hydraulic line 47. The flow is reversed for lowering of the test stand 39.

As shown in FIGS. 3 and 4, the bottle test stand 39 includes an annular bottle supporting surface 48 which is contoured to the shape of the lower side wall of the bottle 18 so that the bottle 18 is supported at the maximum outward peripheral position possible without contacting the bottom or bearing surface of the bottle. This assures that the bottom, the bearing surface and a portion of the lower side wall of the bottle are adequately tested when the test rod 24 engages the central bottom 27 of the bottle. The bearing surface of the bottle, identified as 50 in FIG. 4, is the lowermost annulus of the bottle which normally contacts a flat surface on which it rests. The bottom is the area inside this annulus. It should be noted that the contoured supporting surface 48 of the stand 39 does not reach the bearing surface 50, and in fact is spaced from the bearing surface such that a portion of the curved lower side wall of the bottle is actually included in the test. The remainder of the curved lower side wall is, of course, used to support the bottle by contact with the supporting surface 48, which is preferably covered with a resilient material to spread the support load over maximum area.

It should be understood that although the drawing and much of the discussion herein characterize the bottle testing apparatus as oriented in a vertical direction, this need not be the case. The entire apparatus may be horizontal, with suitable means for guiding the bottle bottom against the test stand. Thus, the terms "up", "down" and "vertical" as used herein and in the claims should be considered to describe directions parallel to the orientation of the bottle, whether the bottle is vertical or not.

In operation of the testing apparatus 17, a bottle 18 is first moved onto the supporting pedestal 41 by a conveying means, the details of which are not shown in FIG. 1. The bottle is positioned as shown in FIG. 3. The test rod 24 is then lowered to a position near but somewhat spaced from the bottom 27 of the bottle and is mechanically locked in position. For the apparatus shown in the figures, the test rod may be locked against upward movement by a pivoted bar 51 connected to the frame 33 of the testing apparatus. When the bar 51 is in the upright position shown in FIG. 4, the test rod 24 is prevented from moving upward beyond the bar. At this point the bottle 18, which has been resting on the pedestal 41, is engaged and raised upward by the test stand 39 with its annular support surface 48. Hydraulic fluid is pumped through the line 43 into the fluid chamber to effect this movement. When the test stand 39 reaches the position shown in FIG. 4, a predetermined pressure continues to be applied in the lower portion 44 of the fluid chamber 37 so that the bottle 18 is pushed upwardly against the bottom tip 28 of the test rod 24 with a predetermined force.

FIGS. 5 and 6 show another means by which certain bottles may be supported for testing by apparatus according to the invention. A testing unit 55 may be structured very similarly to the unit 17, except that it includes a generally C-shaped bottle neck bead support 56 instead of the test stand 39. The support 56 is adapted to engage the neck of a bottle 57 below its neck bead 58. Such large neck beads are often included on large non-returnable soft drink bottles, for handling purposes.

Shown as a variation of the apparatus 17, the testing unit 55 may include a hydraulic lifting and force-applying apparatus 59 similar to the hydraulic cylinder 36 of FIGS. 3 and 4, and adjacent to a contoured bottle positioning pedestal 61. However, instead of supporting a test stand similar to that shown in FIGS. 3 and 4, the hydraulic apparatus 59 is connected by means of structural members 62 with the bottle neck bead support 56. After a test rod 63, identical with the test rod 24 described above, is lowered into the bottle near the bottom and locked into position, the hydraulic apparatus 59 raises the bottle 57 upwardly by its neck bead 58 until the rod 63 contacts the bottle bottom (as shown in dashed lines in FIG. 5), then continues to apply pressure until the bottle is pushed upwardly against the test rod 63 with a predetermined force.

It should be noted that other bottle supporting means may be employed rather than the two types of support shown and described above. For example, an apparatus (not shown) for gripping and frictionally engaging the side wall may be provided.

The force developed by the test apparatus described above introduces a flexure stress into the bottom, bearing surface and lowermost side wall of the bottle which is sufficient to develop a tension stress in the outer surfaces of these areas. As discussed above, the bottle 18 is thus tested for surface and other defects which could cause failure of these portions of the bottle under service conditions wherein high internal pressure is developed. By this testing method, the lower areas of a container are adequately and rapidly tested. In conjunction with a side wall test, the method enables a manufacturer economically to test 100% of the bottles produced. By statistical comparisons with the results of hydrostatic testing, the manufacturer can easily determine the proper force which should be applied in the bottom test to eliminate all bottles whose bottoms could fail if subjected to specific high internal pressures in service.

I claim:

1. A method of testing glass bottles, comprising the steps of:
   subjecting each bottle to a side wall squeeze test, thereby causing the side walls to undergo a tensile stress and causing failure if the side wall has significant defects;
   testing the bottom, bearing surface and lower side wall of each bottle by applying a predetermined force against the inside central bottom of the bottle over a predetermined area thereof, while supporting the bottle at the bottom curve of the side wall, thereby placing the outside surfaces of the bottom, bearing surface and lower side wall in tension and causing failure if significant defects are present.

2. A testing apparatus for determining the stress-withstanding capability of the bottom, bearing surface and lower side wall of a glass container, comprising:
   means for engaging the container peripherally without contacting either of the bottom or the bearing surface;
   a force-applying rod of length sufficient to be inserted in the container mouth and extended to the bottom;
   means for positioning the container mouth in alignment with and adjacent to an end of the force-applying rod;
   means for bringing the engaging means and the force-applying rod toward one another to position the end of the rod in proximity with the inside central bottom of the container; and
   means for continuing the converging movement of the engaging means and the rod until the rod contacts the bottom of the container, and for urging the engaging means and the rod toward one another to produce a bending stress in the bottom, bearing surface and lower side wall of the bottle, whereby the container will fail if significant defects are present.

3. The testing apparatus of claim 2 wherein the end of the force-applying rod includes a resilient yieldable force distributing tip.

4. The testing apparatus of claim 2 wherein the engaging means comprises an annular support positioned to retain the container upright by peripherally engaging the bottom curve of the side wall, said support having an inner resilient surface contoured to the shape of the bottom curve of the container side wall.

5. The testing apparatus of claim 2 wherein said means for continuing the converging movement includes a hydraulic cylinder and a piston connected to the engaging means.

6. The testing apparatus of claim 2 wherein the engaging means comprises means for supporting a neck bead on the container with the container in an upright position.

7. In combination with a side wall squeeze tester for glass containers, an apparatus for testing the bottom, bearing surface and lower side wall of the glass container, comprising:
   means for supporting the container in an upright position by peripheral contact at the bottom curve of the side wall;
   a substantially vertical force-applying rod of length greater than the distance between the top of the container and the inside bottom of the container;
   means for positioning the container mouth directly below the lower end of the force-applying rod;
   means for bringing the supporting means and the force-applying rod together to position the end of the rod in proximity with the inside central bottom of the container; and
   means for continuing the converging movement of the supporting means and the rod until the rod contacts the bottom of the container, and for urging the supporting means and the rod toward one another to produce a bending stress in the bottom, bearing surface and lower side wall of the bottle, whereby the container will fail if significant defects are present.

8. A method for testing the bottom, bearing surface and lower portion of the side wall of a glass container, comprising the steps of:
   supporting the container peripherally without contacting either of the bottom or the bearing surface; and
   applying a predetermined force against the inside central bottom of the container over a predetermined area thereof, thereby developing a tension stress in the outside surfaces of the bottom, bearing surface and lower side wall and causing failure if significant defects are present.

9. The method of claim 8 wherein the supporting step comprises supporting the container at the bottom curve of the side wall, with the container in an upright position.

* * * * *